United States Patent [19]

Hussein et al.

[11] Patent Number: 5,188,634
[45] Date of Patent: Feb. 23, 1993

[54] ROTATABLE LASER PROBE WITH BEVELED TIP

[75] Inventors: Hany M. G. Hussein, Costa Mesa; Marvin Loeb, Huntington Beach; Kenneth M. Galt, Seal Beach, all of Calif.

[73] Assignee: Trimedyne, Inc., Irvine, Calif.

[21] Appl. No.: 553,450

[22] Filed: Jul. 13, 1990

[51] Int. Cl.$^5$ .................................. A61B 17/36
[52] U.S. Cl. .................................. 606/14; 606/15; 606/16; 606/17; 606/7
[58] Field of Search .............. 606/2, 3, 7, 10–18; 128/315–398; 350/96.24, 96.32

[56] References Cited

U.S. PATENT DOCUMENTS

| | | |
|---|---|---|
| 3,498,286 | 3/1970 | Polanyi et al. |
| 3,583,786 | 6/1971 | Marcatilli |
| 3,674,013 | 7/1972 | Polanyi |
| 3,973,828 | 8/1976 | Onoda et al. |
| 4,209,017 | 6/1980 | Shaw |
| 4,346,698 | 8/1982 | Hanson et al. |
| 4,445,892 | 5/1984 | Hussein et al. .............. 606/7 |
| 4,512,762 | 4/1985 | Spears .............. 604/21 |
| 4,566,438 | 1/1986 | Liese et al. .............. 606/16 |
| 4,625,724 | 12/1986 | Suzuki et al. |
| 4,654,024 | 3/1987 | Crittenden et al. |
| 4,740,047 | 4/1988 | Abe et al. .............. 350/96.15 |
| 4,747,405 | 5/1988 | Leckrone .............. 606/7 |
| 4,768,858 | 9/1988 | Hussein .............. 350/96.32 |
| 4,773,413 | 9/1988 | Hussein et al. .............. 606/15 |
| 4,834,093 | 5/1989 | Littleford et al. .............. 128/398 |
| 4,929,246 | 5/1990 | Sinofsky et al. .............. 606/8 |
| 4,950,266 | 8/1990 | Sinofsky et al. .............. 606/2 |
| 5,029,588 | 7/1991 | Yock et al. .............. 606/18 X |

FOREIGN PATENT DOCUMENTS 0153847 2/1984 European Pat. Off.

Primary Examiner—Peter A. Aschenbrenner
Attorney, Agent, or Firm—Dressler, Goldsmith, Shore, Sutker & Milnamow, Ltd.

[57] ABSTRACT

A catheter for ablating obstructing material within a corporal lumen includes a fiber optic member through which radiant energy can be transmitted to a distal end adjacent the site of the obstructing material. Beveled surfaces carried on the distal end of the fiber optic member provide output beams of radiant energy oriented in a direction on the order of 45° with respect to an axis of the member. The laterally deflected radiant energy beams impinge upon regions of plaque or obstructing material in the lumen and have an effective radius greater than the radius of the fiber optic member. By rotating the fiber optic member, a circular locus within the lumen can be ablated or vaporized to create a channel in the lumen with a diameter greater than the diameter of the fiber optic member.

10 Claims, 3 Drawing Sheets

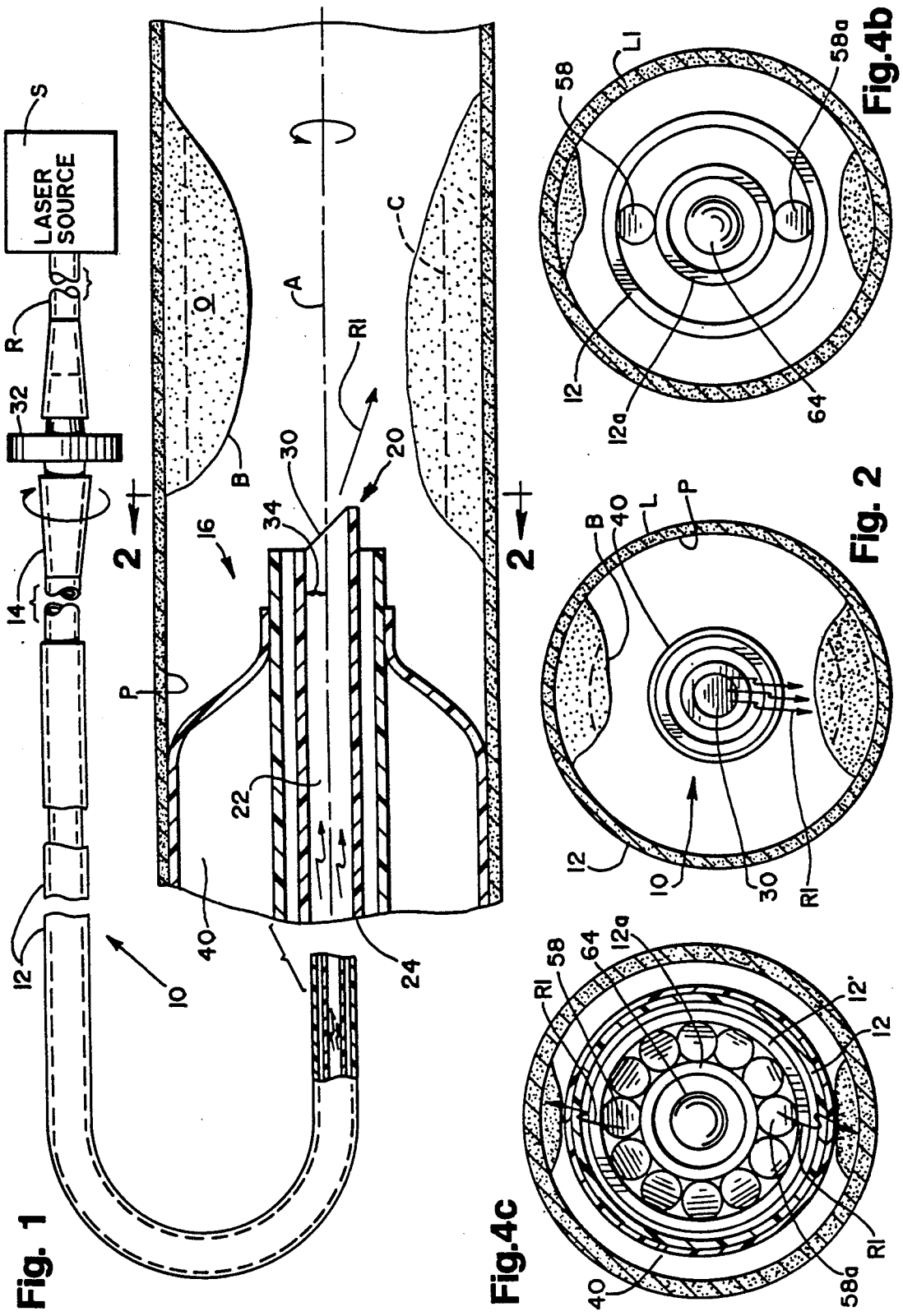

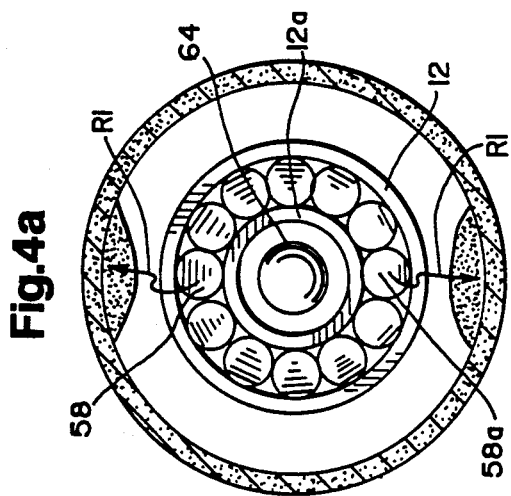
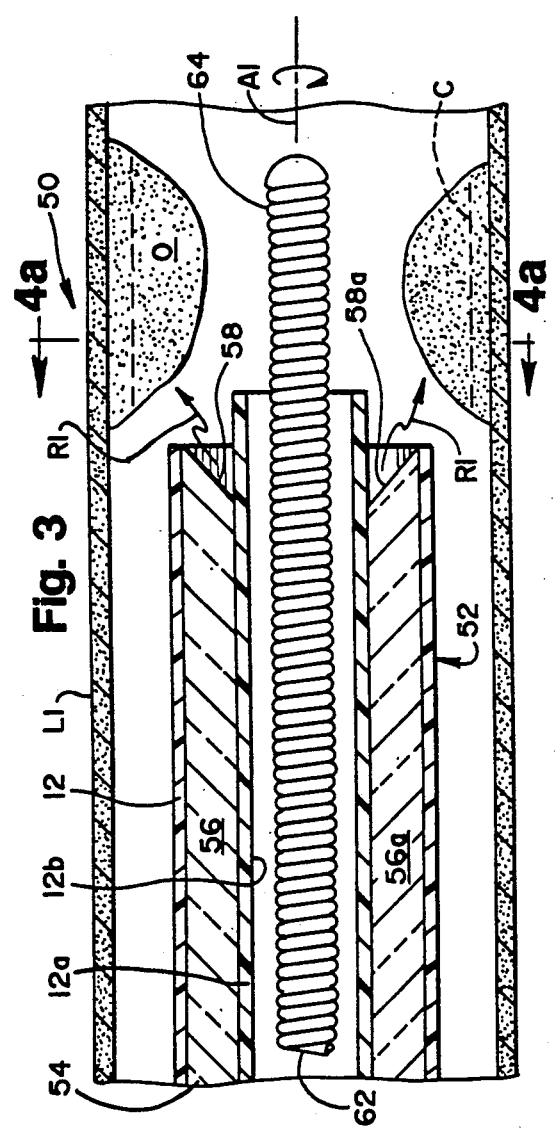
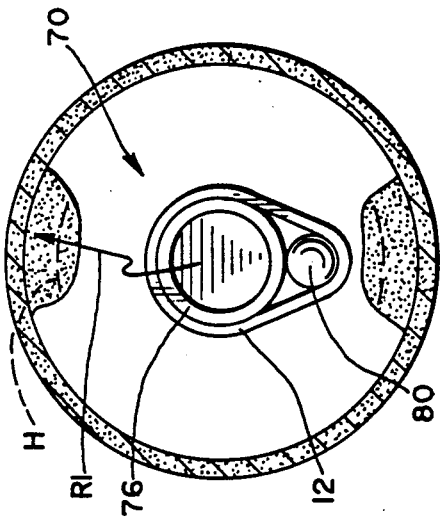
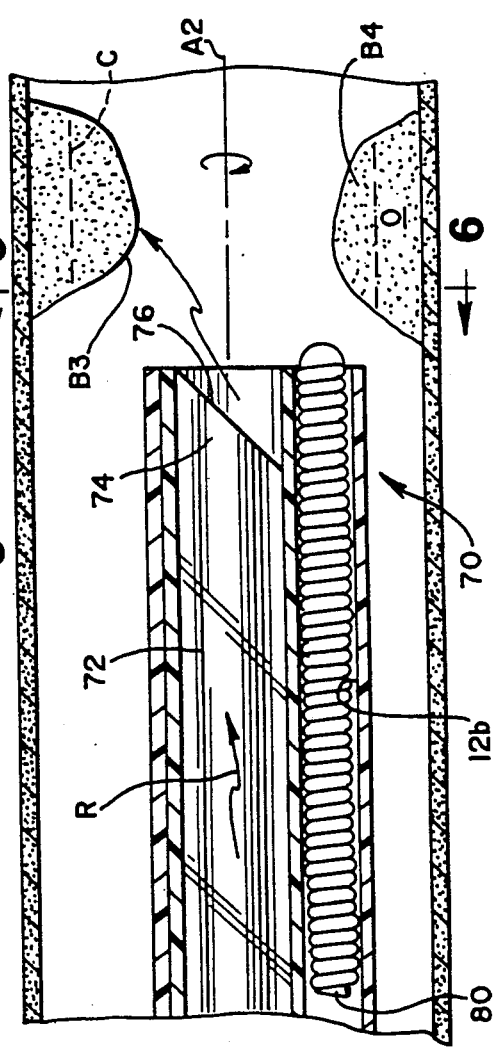

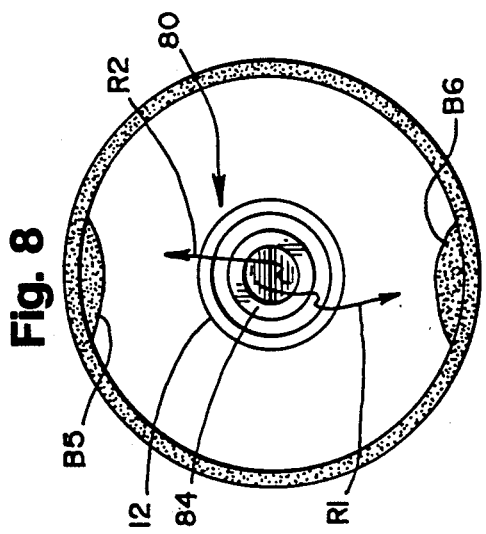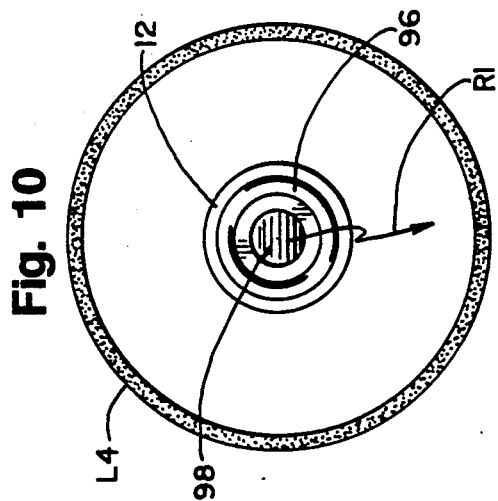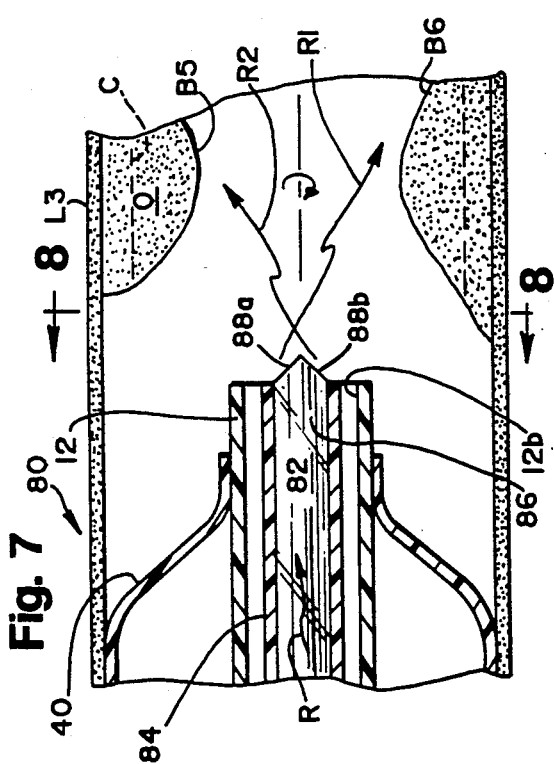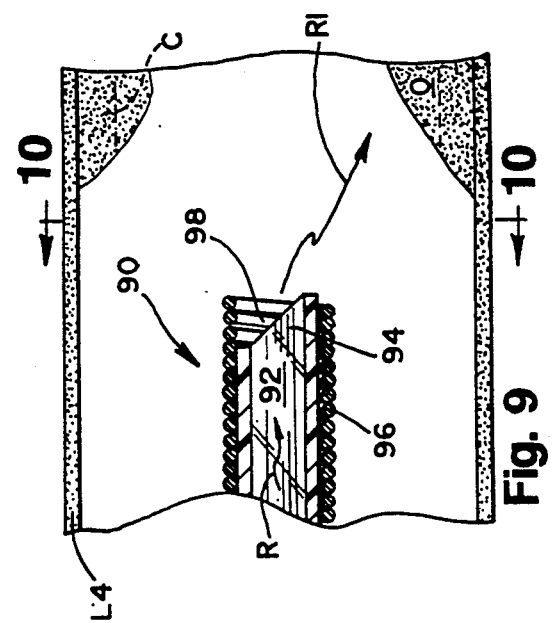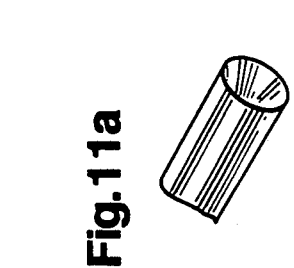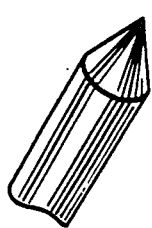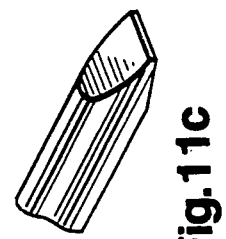

ROTATABLE LASER PROBE WITH BEVELED TIP

FIELD OF THE INVENTION

The invention pertains to radiant energy activated catheters. More particularly, the invention pertains to laser activated catheters for delivering laser energy to internal regions of corporal cavities or lumens such as blood vessels to destroy obstructions therein.

BACKGROUND OF THE INVENTION

Lasers have been used to provide heat, directly or indirectly, for the purpose of removal of plaque or other obstructing materials in a circulatory lumen. One such system is disclosed in Loeb U.S. Pat. No. 4,445,892 (the '892 Patent) entitled "Dual Balloon Catheter Device". Another is disclosed in Hussein et al. U.S. Pat. No. 4,773,413 entitled "Localized Heat Applying Medical Device".

In the system of the Loeb '892 Patent, radiant energy output from a laser is directed by a prism at a 90° to vaporize plaque obstructing a blood vessel. The radiant energy output from the distal end of a fiber optic member is used to directly heat and destroy the obstructing material.

In another embodiment disclosed in the Loeb '892 Patent, the relatively small diameter of the optical fiber produces a similar sized output beam which defines the diameter of the channel made thereby. Lens systems to expand the laser ablation area are not practical for the power density rapidly declines as the area of laser exposure increases.

The noted Hussein et al. Patent discloses the use of an enlarged metallic head mounted at the distal end of the optical fiber. The head is heatable by a beam of laser light. The heated, enlarged head is pressed against the obstructing material to heat and destroy same.

The enlarged head provides a vehicle for creating a flow channel having a diameter greater than the diameter of the heating beam. A heatable head has the disadvantage that the entire head must be heated but only a portion of it is effective as a remover of obstructing material. Hence, a portion of the provided radiant energy does not contribute to making the channel. In addition, the excess heat may damage, in the small arteries, the vessel wall underlying the plaque, or may cause the inner lumen of the vessel to be excessively thrombogenic; although the mechanisms of such phenomena are not yet understood.

While the systems disclosed in the above two patents are useful for the removal of plaque or other obstructing materials, it would be desirable to be able to increase the diameter of the channel being formed by the use of directly applied radiant energy without the need for a lens system and without the need for energy absorbing metal heads.

Laser energy at specific wavelengths, delivered in rapid pulses or continuously, has been shown to destroy tissue and plaque without thermal damage to the vessel wall underlying the plaque. Again, the channel produced is dependent upon the size of the optical fiber.

A number of very small diameter fibers, extended in parallel with one another, can be used to create a usable channel by producing overlapping incident laser energy beams. However, this increases the risk of fiber breakage and incomplete and/or uneven ablation of the obstruction.

In addition, it would be desirable to be able to use rapidly pulsed lasers as energy sources to vaporize obstructions. Pulsed lasers are advantageous in that tissue damage and trauma due to heating can be minimized.

Thus, there continues to be a need to provide a cost effective catheter for direct delivery of radiant energy, such as laser light, onto the surface of plaque or other obstructing material so as to create a channel with a diameter that is larger than the diameter of the beam without diminishing the power density of the beam at the incident area of the obstructing material. In addition, it would be desirable to be able to precisely apply this output radiant energy beam to a selected region within the lumen.

Preferably, the output beam will be directed at least partially ahead and outside of the plane or axis of the distal end of the catheter, so that a channel which is larger than the diameter of the catheter can be formed in a fully occluded lumen. Finally, the catheter should have as small a diameter as possible to facilitate insertion into a vessel and treatment of both large and small lumens.

SUMMARY OF THE INVENTION

A catheter for delivering electromagnetic energy at a predetermined power density to a region within a corporal lumen includes one or more slidable elongated energy conductors, such as fiber optic members, for transmission of the energy from a proximal end to a distal end. A beam deflecting surface is formed on the distal end of the fiber optic members.

Radiant energy transmitted from the proximal end of the fiber optic members to the distal end exits through the deflecting surface at an angle between the leading edge and the axis of rotation of the fiber optic member. The exiting radiation will impinge on a region of the lumen laterally displaced from that axis.

A catheter containing a concentric ring of such fiber optic members will produce an overlapping circle of energy spots resulting in a halo or ring of laser energy at the target tissue.

Rotating the catheter about its central axis, with one or more of the fiber optic members offset from such axis, causes the emitted beam of laser energy to create an arc. Alternatively, rotating the fiber optic members carried concentrically in a catheter also causes the emitted radiant energy to define an arc thereby creating a ring or annular shaped area of incident radiant energy on the affected area.

The ring will have a diameter greater than the diameter of any one of the fiber optic members. The diameter of the ring will also exceed the diameter of the concentric ring of fiber optic members. Since the fiber optic members will transmit verifying amounts of laser energy, rotating the catheter will provide the additional advantage of even distribution of laser energy to the target tissue.

In one embodiment, one or two planar surfaces can be formed on the distal end of a fiber optic member. In another embodiment, a cone shaped convex or concave cavity in a fiber optic member may be used to create a ring shaped area of incident laser energy.

A method of directing a beam of radiant energy to a predetermined displaced area in a corporal lumen with a selected power density includes the steps of forming an elongated beam of electromagnetic energy with the selected power density; transmitting the beam of energy along a central axis toward the area of the lumen to be heated; and deflecting the beam laterally with respect to the central axis adjacent the region to be heated.

The beam will then be incident on a small portion of the region to be heated while the power density remains substantially unchanged. The deflected beam can then be rotated about the central axis thereby forming a generally ring shaped region of incidence of radiant energy on the area of the lumen. The beam can be deflected at an angle on the order of 45° relative to the axis. As the deflected beam is moved axially into the obstructing material, a channel will be formed therein.

Alternately, the beam can be provided radially displaced from but coextensive with a central guide wire. The beam can be rotated about the guide wire. The output radiant energy from the beam will form an arc incident on adjacent obstructing material. The radius of the arc can be greater than the radius of the beam.

In a particular embodiment of the invention, radiant energy generated by a laser can be transmitted along one or more flexible fiber optic members to vaporize an obstruction in the lumen.

The present catheter forms a channel in a lumen larger than the diameter of the catheter. As a result, smaller catheters can be used, reducing mechanical damage to vessels during transit. Further, this catheter does not have a somewhat rigid distal end, as the metal mass of an enlarged heatable head is not present.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 1 is in part, a top elevational view and in part an enlarged fragmentary view, partly in section, of a catheter in accordance with the present invention;

FIG. 2 is an end view taken along plane 2—2 of FIG. 1;

FIG. 3 is a partial, enlarged, sectional view of a distal end of an alternate catheter;

FIG. 4a is an end view taken along plane 4a—4a of FIG. 3;

FIG. 4b is an end view of an alternate form of the catheter of FIG. 3;

FIG. 4c is an end view of another form of the catheter of FIG. 3;

FIG. 5 is a partial, enlarged, sectional view of a distal end of yet another catheter;

FIG. 6 is an end view taken along plane 6—6 of FIG. 5;

FIG. 7 is a partial, enlarged, sectional view of a distal end of yet another catheter;

FIG. 8 is an end view taken along plane 8—8 of FIG. 7;

FIG. 9 is a partial, enlarged sectional view of a distal end of another catheter;

FIG. 10 is an end view of the catheter of FIG. 9 taken along plane 10—10 of FIG. 9; and FIGS. 11a, 11b and 11c each are a fragmentary, enlarged perspective view of an alternate radiant energy emitting fiber optic end region.

DETAILED DESCRIPTION OF THE PREFERRED EMBODIMENT

While this invention is susceptible of embodiment in many different forms, there is shown in the drawings and will be described herein in detail specific embodiments thereof with the understanding that the present disclosure is to be considered as an exemplification of the principles of the invention and is not intended to limit the invention to the specific embodiment illustrated.

A catheter 10 usable for the purpose of vaporizing obstructing material in a circulatory lumen includes an elongated flexible outer sheath. The sheath carries an elongated conductor of radiant energy which has a proximal end and a distal end. The distal end terminates in a beveled tip.

Radiant energy can be injected into the proximal end and transmitted through the fiber optic member to the distal end whereat it exits laterally or at an angle with respect to an axis of the catheter. Rotating the beveled tip directs the emitted radiation onto an annular region of obstructing material. The annular region has a radius greater than the radius of the fiber optic member.

With respect to FIG. 1, the catheter 10 has an exterior flexible sheath or housing 12. The sheath 12 has a proximal end 14 and a distal end 16 illustrated positioned in a lumen L. Coupled to proximal end 14 is a laser source S.

Radiant energy R output from the laser source S can be injected into the proximal end 14. The sheath 12 carries, rotatably mounted therein, a conductor of electro-magnetic energy 20.

In the embodiment of FIGS. 1 and 2, the conductor 20 is formed as a single fiber optic member 22 which carries an exterior cladding 24, which can be a commercially available coating, such as a silicon rubber, or, to provide greater strength to the fiber during rotation, a thin metal coating, such as aluminum. The fiber optic member 22 is rotatably mounted within the sheath 12.

Fiber optic member 22 terminates at a beveled end surface 30 which is oriented at an acute angle with respect to a central axis of rotation A of the member 20. The conducting member 20 can be rotated by means of a rotatable member 32 carried adjacent the proximal end 14.

As is illustrated in FIG. 1, radiant energy $R_1$ output from the surface 30 is directed laterally with respect to the axis of rotation A. As a result, the radiant energy $R_1$ is incident on a surface B of the obstructing material O which is displaced laterally with respect to the axis A, a distance greater than a radius 34 of the conductor 20.

Hence, when the conductor 20 is rotated about the axis A, an annular region of the material O is vaporized. This annular region has a radius which is greater than the radius 34. As a result, by advancing the distal end 16 toward the obstructing material O, a larger channel can be formed with the catheter 10 than can be formed with the beam of laser energy merely exiting axially from fiber optic member 22.

A further advantage of the catheter 10 is that the laterally directed radiant energy $R_1$ impinges upon the surface B with substantially the same energy density as it has when it exits the proximal end of the optical fiber member. The region B is subjected to very intense controllable radiant energy $R_1$ such that channel C (illustrated in phantom) can be cut through the obstructing material O by rotating the conductor 20 while simultaneously advancing the surface 30 axially through the lumen L. The degree of removal or diameter of the channel C which is being cut can be readily controlled by varying the input energy from the laser source S, the speed of forward movement and/or the speed of rotation of conductor 20.

If desired, the distal end 16 can also carry an inflatable balloon 40 which can be used to occlude the lumen L during the obstruction removal procedure. It will also be understood that an additional conduit could be provided within the sheath 12 for the purpose of expanding the balloon 40. Another conduit can be provided in the sheath 12 for the purpose of infusion of a fluid, such as saline, an oxygenated fluid (Flousol ™), or an inert gas, such as carbon dioxide. The same channel or a separate channel may be used for suctioning or withdrawing material from the lumen L.

The surface 30 can be oriented at an angle substantially equal to 45° with respect to the axis of rotation A. It will also be understood that the surface need not be formed as a completely planar surface. It could be formed such that it is at least in part curved.

If carbon dioxide is injected with the lumen L adjacent to the obstruction O, and if the angle of the surface 20 with respect to the axis A is on the order of 43°, then the emitted radiant energy $R_1$ will exit with the orientation illustrated in FIG. 1. In this embodiment, at an axial distance of 1 mm from the center 30a of beveled face 30, the exiting radiation $R_1$ should impinge on the surface B on the order of 1 mm radially displaced from the axis A. Rotating the output surface 30 will produce a locus of incident area with a diameter on the order of 2 mm.

It will be understood that the angle at which the emitted radiation exits from the beveled end surface 30 will be affected by the angle the surface 30 makes with the axis A, the index of refraction of the fiber optic member 22 as well as the index of refraction of the fluid in the lumen L. Such variations are within the spirit and scope of the present invention.

In a further embodiment, sheath 12 can be made of a transparent polyethylene, polyvinyl or polyurethane chloride material which is optically transparent to laser energy of the appropriate wavelength. Balloon 40 can be made of optically transparent latex or silicon rubber. The fluid used to inflate balloon 40, such as $CO_2$, saline or an oxygen bearing fluid, is also optically transparent to laser energy at such wavelengths. By rotating fiber optic member 22 within the balloon 40, laser energy can be applied to soften the plaque while said plaque is being compressed by balloon 40, reducing the incidence of desection and flaps and leaving a smoother inner lumen L.

FIGS. 3, 4a and 4b illustrate alternate forms of catheter 50 which can be utilized to create a channel having a diameter greater than the diameter of the radiant energy conductor carried therein. The catheter 50, illustrated positioned in a lumen $L_1$, in FIG. 3 has an exterior sheath, corresponding to the exterior sheath 12; a proximal end, not illustrated in FIG. 3; and a distal end 52.

The sheath 12 carries one or more fiber optic members 56 and 56a displaced radially and eccentrically from the central axis $A_1$ of catheter 50. An elongated interior sheath 12a forms a hollow cylindrical channel 12b which enables catheter 50 to be slidably advanced over guide member 64 through the lumen of the vessel to the obstruction.

The distal ends of fiber optic members 56 and 56a terminate in radiant energy emitting surfaces 58 and 58a, which surfaces are oriented at a selected acute angle with respect to a central axis of rotation $A_1$.

In one embodiment, illustrated in FIG. 4(a), a concentric ring of beveled fiber optic members can, but need not be, rotatably mounted with respect to guide member 64.

In another embodiment, fiber optic member 56 can, but need not be rotatably mounted with respect to the guide member 64. If rotated about guide member 64, fiber optic member 56 describes an arc and creates a cylindrical region of incidence on obstructing material O with a radius greater than a radius of catheter 50.

Hence, the output radiant energy is deflected at an angle such that upon rotation a conical locus having a half angle equal to the angle of deflection of the beam with respect to the axis of rotation $A_1$ is formed. This conical locus is laterally displaced with respect to the axis of rotation $A_1$ and will form a channel C, illustrated in phantom in FIG. 4, in the obstructing material O having a radius greater than the radius of the fiber optic member. As a result, a larger diameter channel can be formed through the obstructing material O. The output radiant energy beam has an energy density corresponding substantially to the energy density of the individual fiber optic members 56 and 56a.

In yet another embodiment of a catheter illustrated in FIG. 4c, an interior sheath 12' surrounds a plurality of fiber optic members including members 58 and 58a. The exterior sheath 12 surrounds the interior fiber optic carrying sheath 12' and also carries expandable balloon 40.

In the embodiment of FIG. 4c, the exterior sheath 12 and the interior sheath 12' are formed of material optically transparent to the desired wavelength of laser energy. Balloon 40 can be made of latex or other expandable materials which are optically transparent to laser energy of the desired wavelength. If desired, the interior sheath 12' could be partly covered with a flexible metallic sheath to resist radial forces that result from inflating balloon 40 and compressing plaque in the lumen.

The plurality of fiber optic members 56 and 56a can be moved forward or backward, laterally while being rotated within the sheath 12' subsequent to inflation or partial inflation of the balloon 40. Thus, laser energy exiting the members 58 and 58a can be used to soften the plaque at the same time while the plaque is being compressed or, if partially inflated, held in place in an extended position by the balloon 40, resulting in a smoother inner lumen L.

Assuming sufficient overlap of the incident regions associated with each of the members 58 or 58a, the plurality of fiber optic members within the sheath 12' may not have to be rotated and can simply be moved laterally within sheath 12.

Another form of catheter 70 is illustrated in FIG. 5. The catheter 70 carries an eccentrically located conductor of radiant energy 72.

At a distal end 74, the radiant energy conductor 72 terminates in a single bevel, so as to direct the laser energy away from guide member 80.

A guide member 80 can be provided offset with respect to the rotatably mounted energy conductor 72 over which catheter 70 can be advanced through the lumen of the vessel to the target tissue and, if desired, rotated about said guide member 80. If conductor 72 is rotated, catheter 70 creates a channel C, illustrated in phantom in FIG. 5, through the obstructing material O with a diameter greater than the diameter of the fiber optic member 72.

In an alternate embodiment to FIG. 5, not illustrated, the distal end of conductor 72 can be beveled in two planes to form two emitting surfaces. The use of first and second surfaces results in first and second regions or incidence $B_3$ and $B_4$ displaced laterally with respect to the axis $A_2$ which can then be formed into an annular locus of incident radiant energy thereby producing the channel C in the lumen $L_2$. Thus, by rotating the conductor 72, a channel C can be cut through the obstructing material O with a diameter that is greater than the diameter of the member 72.

It will be understood that the catheters 50 and 70 could also be combined with expandable occluding balloons such as the balloon 40. It will also be understood that the surface 76 could be curved rather than planar if desired. The annular heated region H which results when the fiber optic conductor 72 is rotated is illustrated in phantom in FIG. 6.

If the sheath 12 and balloon 40 are constructed of a material optically transparent to laser energy, member 82 may be rotated within balloon 40 to soften plaque while balloon 40 is inflated, to reduce cracks, fissures and flaps, prevent desection and leave a smoother lumen L.

FIGS. 7 and 8 illustrate another alternate catheter 80. In the catheter 80, the flexible elongated housing 12 defines an interior lumen 12b. A slidable and, if desired, rotatable fiber optic member 82 is carried within the lumen 12b. The lumen 82 can be coupled to the laser source S at proximal end 14 not illustrated in FIG. 7. The fiber optic member 82 is encased in cladding 84 of a conventional variety.

The member 82 terminates at a distal end 86 in first and second convex beveled surfaces 88a and 88b. Radiant energy $R_1$ output from surface 88a and radiant energy $R_2$ output from surface 88b is incident upon regions $B_5$ and $B_6$ of obstruction O in lumen $L_3$. The convex emitting surfaces 88a and 88b emit the corresponding radiant energy $R_1$ and $R_2$ laterally at an acute angle with respect to a central axis. That radiant energy is incident upon regions $B_5$ and $B_6$ and is effective to ablate and vaporize obstructing material O thereby forming a channel C, illustrated in phantom, having a radius greater than the radius of the member 82.

It will be understood that the convex beveled surfaces 88a and 88b could be replaced with a convex cone or with a concaved, cone shaped inner surface, as illustrated in FIGS. 11a and 11b, without departing from the spirit and scope of the present invention.

FIGS. 9 and 10 illustrate an alternate embodiment of a laser guidewire 90 positioned in a lumen $L_4$. The laser guidewire 90 includes an exterior elongated flexible guidewire member 96 containing in its central lumen a fiber optic conducting member 92. The member 92 can be coupled at a proximal end, not illustrated, to the laser source S. At a distal end 94, the fiber optic member 92 terminates in a beveled emitting surface 96.

Radiant energy $R_1$ emitted from the surface 98 of the fiber optic member impinges upon obstructing material O in the lumen $L_4$ vaporizing and ablating same. The radiant energy $R_1$ exits from the surface 98 at an acute angle with respect to a central axis of the fiber optic member 92.

The guidewire member 96 or, alternatively, fiber optic member 92, can be rotated as previously discussed for creating a channel C, illustrated in phantom in FIG. 9 in the obstructing material O, which will have a radius greater than the radius of guidewire member 96. Fiber optic member 92 can also contain two planar surfaces or be concave or convex, as shown in FIG. 11a, 11b and 11c. As shown in FIG. 10, an inflatable balloon $L_4$ surrounds sheath 12 with which laser guidewire 90 can be moved laterally. Inflating the balloon $L_4$ with a fluid having a proper refractive index, such as carbon dioxide may further deflect the laser beam laterally to assist in achieving a 90° divergence from the longitudinal axis of fiber optic member 92.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. An apparatus for delivering radiant energy at a predetermined power density to a displaced region comprising:

at least one elongated, optical conductor of radiant energy of a selected radius having a proximal end and a distal end with a cross section of a predetermined area wherein radiant energy injected into said proximal end exits at said distal end;

an elongated housing having a central axis and with said conductor carried thereby for rotation relative to said housing about said axis; and a first beveled deflecting surface integrally formed on said distal end, adapted to deflect and cause said radiant energy to exit said surface laterally with respect to said axis; and a second beveled deflecting surface integrally formed on said distal end but displaced from said surface, adapted to deflect and cause said radiant energy to exit said second surface laterally with respect to said axis;

whereby rotation of said optical conductor about said axis forms a first locus of incidence on the region with a radius greater than said selected radius and a second locus of incidence on the region displaced laterally from said first locus.

2. An apparatus as in claim 1 with said first surface being planar and integrally formed in said distal end.

3. An apparatus as in claim 1 with said first surface and said second surface oriented at a selected angle with respect to said axis.

4. An apparatus as in claim 1 with said first and second surfaces oriented so as to direct energy onto first and second regions, displaced from said axis.

5. An apparatus as in claim 1 including a guide wire carried within said housing.

6. An apparatus as in claim 5 with said guide wire centrally located in said housing.

7. A guidable endoscope for ablating obstructing material in a corporal lumen comprising:

a flexible, elongated housing;

a guide wire longitudinally slidably received by said housing and coextensive therewith;

a radiant energy transmitting member carried within said guide wire by said housing, said transmitting member having a proximal end and a distal end with said distal end carrying a beveled transmissive end region; and a member carried by said housing adjacent said proximal end for rotating said transmitting member about a selected axis.

8. A guidable endoscope as in claim 7 including an inflatable balloon carried on said housing adjacent said distal end.

9. A guidable endoscope as in claim 4 with said transmitting member displaced laterally with respect to said guide wire and rotatable thereabout.

10. A guidable endoscope as in claim 7 including means for coupling said proximal end to a source of radiant energy.

* * * * *